United States Patent [19]
Humora et al.

[11] Patent Number: 5,539,126
[45] Date of Patent: Jul. 23, 1996

[54] METHOD FOR PREPARING HOMOCHIRAL MALEIMIDE INTERMEDIATES, VIA SILYLATION TECHNIQUES

[75] Inventors: Michael J. Humora, Cranbury; Richard H. Mueller, Ringoes; Janak Singh, Lawrenceville; Yadagiri Pendri, Matawan, all of N.J.

[73] Assignee: Bristol-Myers Squibb Company, Princeton, N.J.

[21] Appl. No.: 230,570

[22] Filed: Apr. 20, 1994

[51] Int. Cl.$^6$ .................. C07D 207/448; C07D 207/452
[52] U.S. Cl. ............................................ 548/545; 548/548
[58] Field of Search ...................... 548/545, 548

[56] References Cited

U.S. PATENT DOCUMENTS 5,164,461  11/1992  Mitchell et al. ..................... 525/478
5,194,627   3/1993  Shinohara et al. ................... 548/406

OTHER PUBLICATIONS

Myers, A. I. et al, "A Facile Synthesis of Chiral Bicyclic Lactams Utilized in the Formation of Chiral Quaternary Carbon Compounds", J. Org. Chem. 1989, 54, 4243–4256.
Davis, P. D. et al, "A Mild Conversion of Maleic Anhydrides Into Maleimides", Tetrahedron Letter, vol. 31, No. 36, pp. 5201–5204, 1990.
Keller, O. et al, "Preparation and some Properties of Maleimido Acids and Maleoyl Derivatives of Peptides", Hellvetica Chimica Acta, vol. 58, Fasc. 2 (1975), Nr. 62–62, 531–541.
Hartman, G. D. et al, "Iminium Ion Mediated Cyclizations of 4–Aryl–1, 4–dihydropyridines, Bridging with Acetals, Carbonyls, and Thiocarbonyls", J. Org. Chem. 1985, vol. 50, pp. 2423–2427.
Miller, S. A. et al, "Highly Selective Formation of Cis–Substituted Hydroxylactams via Auxiliary–Controlled Reduction of Imides", J. Org. Chem., 1989, vol. 54, pp. 2502–2504.
Mukaiyama, T. et al, "An Asymmetric Synthesis of Bicyclic Lactones and its Application to the Asymmetric Synthesis of (1R,3S)–cis–Chrysanthemic Acid", Chemistry Letters, 1983, pp. 385–388.
Organic Syntheses Collective vol. 4, 1951, pp. 327–329.
Braish, T. F. et al, "A Practical Synthesis of N–Substituted Maleimides", Synlett, Dec. 1992, pp. 979–890.
Rangnekar, V. M. et al, "Synthesis of N–Aryl/substituted––methyl/heteroaryl–α–pyrrolidino/peperidino Succinimides as Antituberculosis Agents", Indian Journal of Chemistry, vol. 22B Oct. 1982, pp. 1070–1071.
Aoyama T. et al, "Preparation of N–arylmaleimides", Chem. Abstracts, vol. 118, 1993, p. 982.
Cava, M. P. et al, "N–Phenylmaleimide", Organis Synthesis, vol. 41, pp. 93–94.
Nielsen, O. et al, "Facile Synthesis of Reagents Containing a Terminal Maleimido Ligand Linked to an Active Ester", Synthesis, Oct. 1991, pp. 819–821.

Primary Examiner—David B. Springer
Attorney, Agent, or Firm—Burton Rodney

[57] ABSTRACT

A method is provided for preparing homochiral maleimide intermediates of the structure

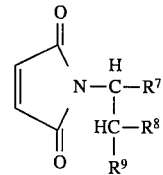

wherein $R^7$, $R^8$ and $R^9$ are as defined herein by reacting a homochiral amine of the structure

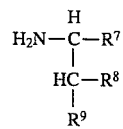

with maleic anhydride and a silylating agent. The maleimide intermediate is used in the enantio-selective preparation of thromboxane $A_2$ receptor antagonists.

9 Claims, No Drawings

METHOD FOR PREPARING HOMOCHIRAL MALEIMIDE INTERMEDIATES, VIA SILYLATION TECHNIQUES

FIELD OF THE INVENTION

The present invention relates to methods for preparing homochiral maleimides from homochiral amines and maleic anhydride employing silylation techniques. The resulting maleimides may be employed to prepare enantioselectively a 7-oxabicycloheptane carboxylic acid prostaglandin analog for use as an anti-thrombotic—anti-vasospastic product.

BACKGROUND OF THE INVENTION

U.S. Pat. No. 5,100,889 to Misra et al discloses 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic diseases, and have good duration of action. Examples of compounds disclosed in Misra et al have the structural formula

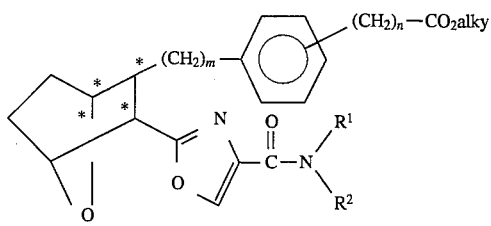

and including all stereoisomers thereof, wherein
m is 1, 2 or 3; n is 0, 1, 2, 3 or 4;
$R^1$ is hydrogen, lower alkyl, aralkyl, aryl, cycloalkyl, cycloalkylalkyl, or amide

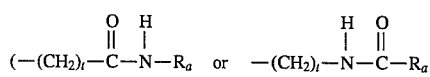

wherein t is 1 to 12 and $R_a$ is lower alkyl, aryl, cycloalkyl, or cycloalkylalkyl);
$R^2$ is hydrogen, lower alkyl, aryl, or aralkyl; or $R^1$ and $R^2$ together with the nitrogen to which they are linked may form a 5- to 8-membered ring.

Misra et al disclose that these compounds may be prepared by transmetallating bromophenylalkyl A

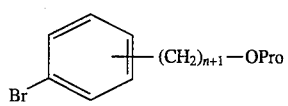

by treatment with $t-C_4H_9Li$ or $n-C_4H_9Li$ or subjecting A to a Grignard reaction by treatment with Mg, and then condensing with perhydrobenzofuran-1-ol B

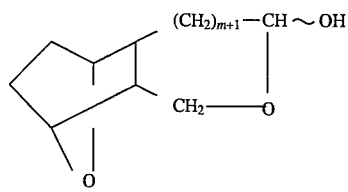

to form the condensed 7-oxabicycloheptane alcohol compound of the structure C

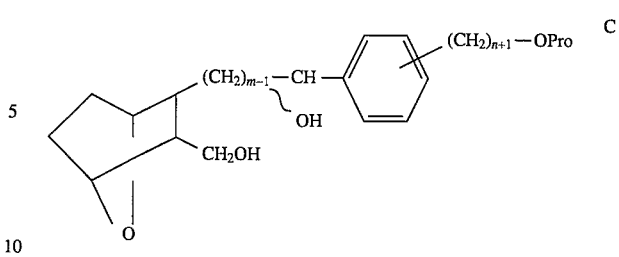

and then subjecting the condensed compound to hydrogenolysis to form the following alcohol

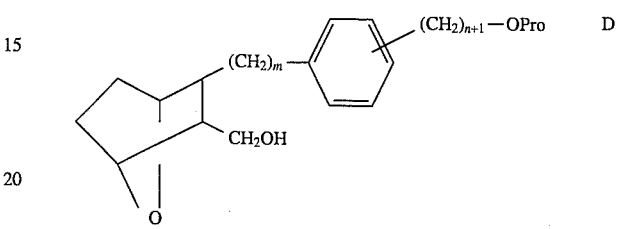

Where Pro is thexyldimethylsilyl or t-butyldimethylsilyl, the alcohol is acetylated and the silyl protecting group of the so-formed acetate is removed to form the following acetate:

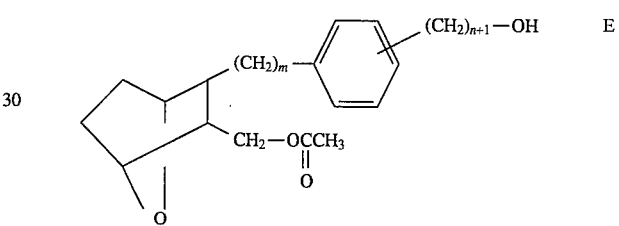

which is treated with a protecting compound and the acetate is removed by treatment with aqueous hydroxide or excess methyllithium to form the following alcohol:

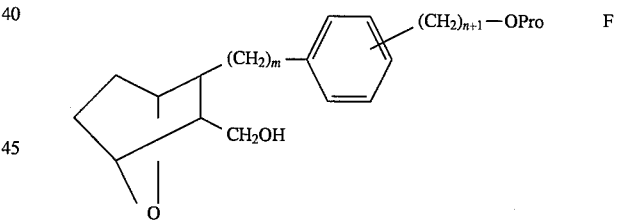

(where Pro is t-butyldiphenylsilyl).

The protected alcohol is subjected to a Jones oxidation to form the following acid:

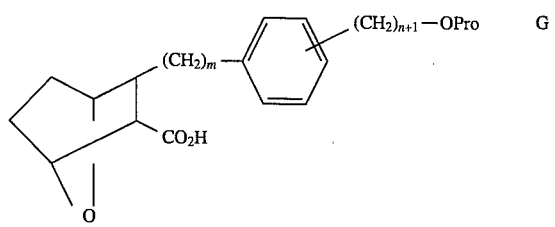

The so-formed carboxylic acid intermediate is then employed to make the final compound.

In a more preferred procedure, Misra et al disclose protecting the alcohol function of alcohol C to form the protected alcohol

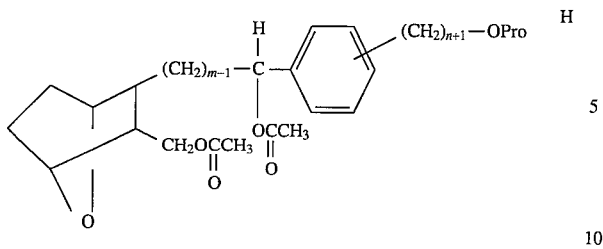

subjecting the protected alcohol H to a Jones oxidation and esterification to form the ester

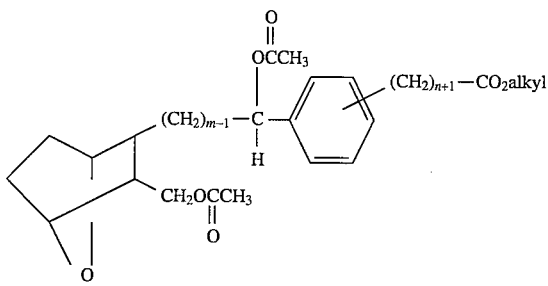

which is made to undergo hydrogenolysis and subsequent removal of the acetate protecting group by transesterification to afford the alcohol

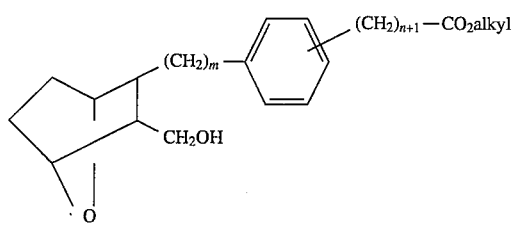

which is subjected to a Jones oxidation to form the carboxylic acid intermediate L

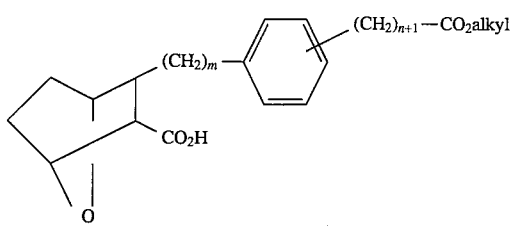

In an alternative procedure where n is 1, the above carboxylic acid intermediate L is formed by treating F (n=2) with acetic anhydride and removing the protecting group to form the acetate alcohol

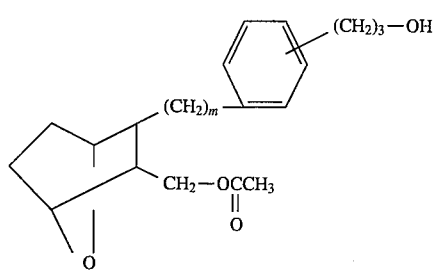

which is made to undergo a Dess-Martin oxidation to form the aldehyde

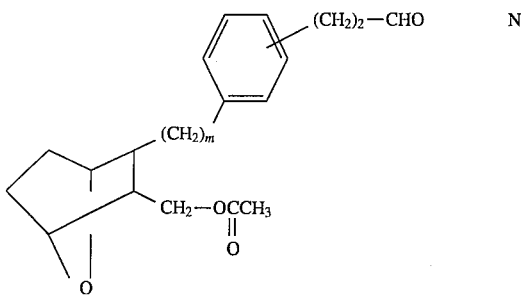

The above aldehyde is oxidized and esterified to the corresponding acetate ester, deprotected, and subjected to a Jones oxidation to form carboxylic acid L where n is 1.

DESCRIPTION OF THE INVENTION

In accordance with the present invention, methods are provided for preparing homochiral maleimide intermediates for use in the enantioselective preparation of 7-oxabicycloheptyl substituted oxazole amide prostaglandin analogs as described hereinafter which are useful as anti-thrombotic and anti-vasospastic compounds.

Thus, in one aspect of the invention, a method is provided for preparing a chiral maleimide intermediate of the structure

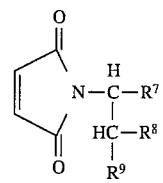

wherein $R^7$ is aryl or lower alkyl,
$R^8$ is H, aryl or lower alkyl, and
$R^9$ is H, OH or lower alkyl, which includes the steps of
(a) providing an amine of the structure

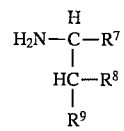

wherein $R^7$, $R^8$ and $R^9$ are as defined above, and
(b) treating the amine with maleic anhydride, a silylating agent and an organic base, such as an amine base, to form the maleimide intermediate I.

The starting amine II will preferably be a chiral amine of the structure

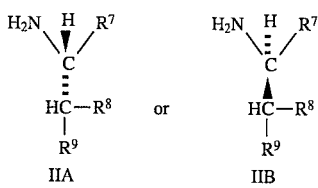

so that maleimide intermediate I formed will have a single chiral center as shown:

[Structures IA and IB shown]

In another embodiment of the present invention, a method is provided for preparing a maleimide intermediate of the structure

[Structure III shown with N—C(H)(R$^7$)—CH(R$^8$)(OCAlkyl)(=O)]

wherein R$^7$ is aryl or lower alkyl, which includes the step of (a) providing an amine of the structure

[Structure IIC: H$_2$N—C(H)(R$^7$)—CH(R$^8$)—OH]

wherein

R$^7$ is aryl or lower alkyl, and

R$^8$ is H, aryl or lower alkyl, (b) treating the amine with a silylating agent and maleic anhydride to form silylated compound of the structure

[Structure IV shown]

and (c) treating the silylated compound with water, a desilylating agent, a cyclizing agent, and an organic base to form the maleimide intermediate.

The starting amine IIC will preferably be a chiral amine of the structure

[Structure IID shown]

wherein R$_7$ is preferably phenyl and R$^8$ is preferably H. The chiral amine IIC is treated with a silylating agent, preferably 1,3-bis(trimethylsilyl)urea, and the reaction mixture is treated with maleic anhydride, to form the silylated compound which preferably is

[Structure IVA shown]

The silylated compound is treated with water, desilylating agent, preferably tetrabutylammonium fluoride, cyclizing agent, preferably acetic anhydride and base, preferably triethylamine to form the maleimide intermediate of the structure

[Structure IIIA shown]

In a still further aspect of the present invention, a method is provided for preparing an oxazole acid of the structure

[Structure V shown]

wherein R$^1$ is hydrogen, lower alkyl, aryl, aralkyl, cycloalkyl, cycloalkylalkyl, or an amide of the structure $$-(CH_2)_t-\overset{O}{\underset{}{C}}-\overset{H}{\underset{}{N}}-R_a \quad \text{or} \quad -(CH_2)_t-\overset{H}{\underset{}{N}}-\overset{O}{\underset{}{C}}-R_a$$

wherein t is 1 to 12 and R$_a$ is lower alkyl, aryl, cycloalkyl or cycloalkylalkyl;

R$^2$ is hydrogen, lower alkyl, aryl, or aralkyl; or

R$^1$ and R$^2$ together with the N to which they are linked form a 5- to 8-membered ring which contains only the single N heteroatom;

or esters thereof or pharmaceutically acceptable salts thereof, which includes the steps of forming a maleimide intermediate of the structure

[Structure I shown]

(employing the methods of preparation as described above), reacting the above imide with furan in the presence of a Lewis acid to form an imide of the structure

[Structure VI shown]

reducing the imide VI by reacting the imide VI with hydrogen in the presence of a reduction catalyst to form the imide intermediate

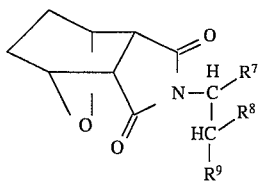
VII and employing the imide intermediate VII to form the oxazole acid, ester thereof or pharmaceutically acceptable salt thereof.

In a further aspect of the present invention, a method is provided for preparing an oxazole acid of the structure

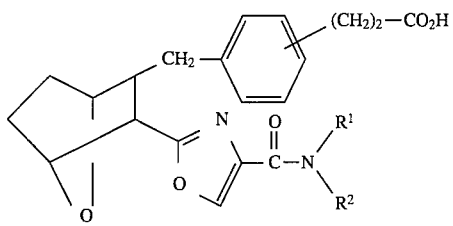
V wherein $R^1$ and $R^2$ are as defined above, or esters thereof or pharmaceutically acceptable salts thereof, which includes the steps of forming an ester compound of the structure

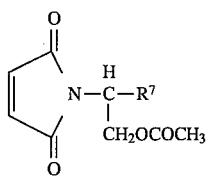
IIIB (according to the method as described above), treating the ester compound with furan to form a compound of the structure

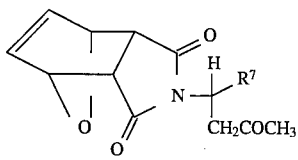
VIA treating the above compound with $H_2$ in the presence of a hydrogenation catalyst to form an ester of the structure

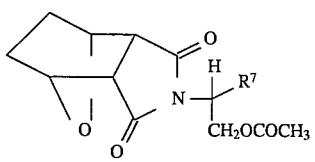
VIIA treating the alcohol with $H_2$ in the presence of a reduction catalyst and then deacetylating with $K_2CO_3$ or other salt and alcohol to form the imide intermediate of the structure

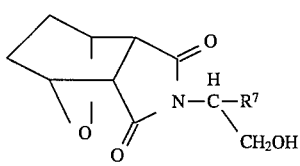
VIIB and employing the imide intermediate to form an oxazole acid, ester thereof or pharmaceutically acceptable salt thereof.

DETAILED DESCRIPTION OF THE INVENTION

The methods of the invention are outlined in Reaction Schemes 1 to 5 set out hereinafter.

Reaction Scheme 1
Preparation of Chiral Maleimide Intermediate I

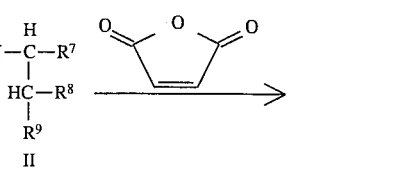
II

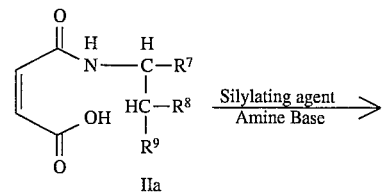
IIa

Silylating agent / Amine Base →

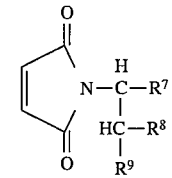
I wherein
$R^7$ is aryl or lower alkyl,
$R^8$ is H, aryl or lower alkyl and
$R^9$ is H, OH or lower alkyl.

Referring to Reaction Scheme 1, in accordance with the present invention, a method for preparing a maleimide intermediate I is provided wherein amide acid IIa is subjected to a silylation reaction by treating IIa with a silylating agent in the presence of an organic base, and an organic solvent such as acetonitrile, n-butyl acetate or toluene, to form maleimide intermediate I.

The amide acid IIa is prepared by reacting amine II with maleic anhydride

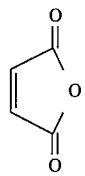

in the presence of acetonitrile, tetrahydrofuran (THF), ethylacetate or other inert organic solvent such as described above, employing a molar ratio of maleic anhydride:II of within the range of from about 0.9:1 to about 1.05:1, preferably about 1:1.

Starting amine II will preferably be in chiral form IIA or IIB so that the final maleimide intermediate I will be in chiral form IA or IB.

Examples of silylating agents useful in the above reaction include, but are not limited to, 1,1,1,3,3,3-hexamethyldisilazane (HMDS), chlorotrimethylsilane (TMSCl), or bistrimethylsilylurea (BSU), bistrimethylsilylacetamide (BSA), preferably HMDS.

Examples of organic bases suitable for use in the above reaction include, but are not limited to, amine bases such as diisopropylamine, triethylamine, diisopropylethylamine or tributylamine.

In carrying out the above reactions shown in Scheme 1 to form maleimide I, the amine base will be employed in a molar ratio to amide acid IIa of within the range of from about 1.2:1 to about 1.1:1, preferably about 1:1, while the silylating agent is employed in a molar ratio to amide acid IIa of within the range of from about 2:1 to about 1:1, preferably from about 1.8:1 to about 1.4:1. The reaction is carried out at a temperature within the range of from about 60° to about 110° C., preferably from about 70° to about 100° C.

Referring to Reaction Scheme 2, in accordance with the present invention, a method for preparing maleimide intermediate Ia is provided wherein amine alcohol IIC (which includes at least one chiral center, and $R^7$ is preferably phenyl) is reacted with a silylating agent and maleic anhydride in the presence of an inert organic solvent such as THF, toluene, glycine, acetonitrile or ethylacetate, at a temperature within the range of from about 45° to about 85° C., preferably from about 50° to about 70° C., to form silylated compound IV which is cyclized by treatment with water and a desilylating agent (also referred to as a catalyst for desilylation) such as n-tetrabutyl ammonium fluoride (TBAF), potassium fluoride or cesium fluoride, in the presence of a cyclizing agent, such as an acid anhydride like acetic anhydride, or propionic anhydride, and an amine base such as triethylamine, tributylamine or diisopropylamine, to form maleimide intermediate Ia. The above reactions are carried out at a temperature within the range of from about 50° to about 70° C., preferably from about 55° to about 65° C.

Examples of silylating agents and amine bases suitable for use herein include any of those set out about with respect to Scheme 1 and preferably are bistrimethylsilylurea (BSU) as the silylating agent and triethylamine as the amine base.

In carrying our the above reaction shown in Scheme 2 to form maleimide Ia, the silylating agent will be employed in a molar ratio to amine alcohol IIC of within the range of from about 2.5:1 to about 5:1, preferably from about 3:1 to about 4:1, while the maleic anhydride is employed in a molar ratio to amine alcohol IIC of within the range of from about 0.75:1 to about 3:1, preferably from about 1:1 to about 2:1.

The desilylating agent, such as TBAF, will be employed in a molar ratio to silylated acid compound IV of within the range of from about 0.05:1 to about 0.3:1, preferably from about 0.1:1 to about 0.2:1, while the cyclizing agent, such as the acid anhydride will be employed in a molar ratio to silylated acid compound IV of within the range of from about 5:1 to about 20:1, preferably from about 7:1 to about 10:1, and the base will be employed in a molar ratio to silylated acid compound IV of within the range of from about 5:1 to about 15:1, preferably from about 1 to about 10:1.

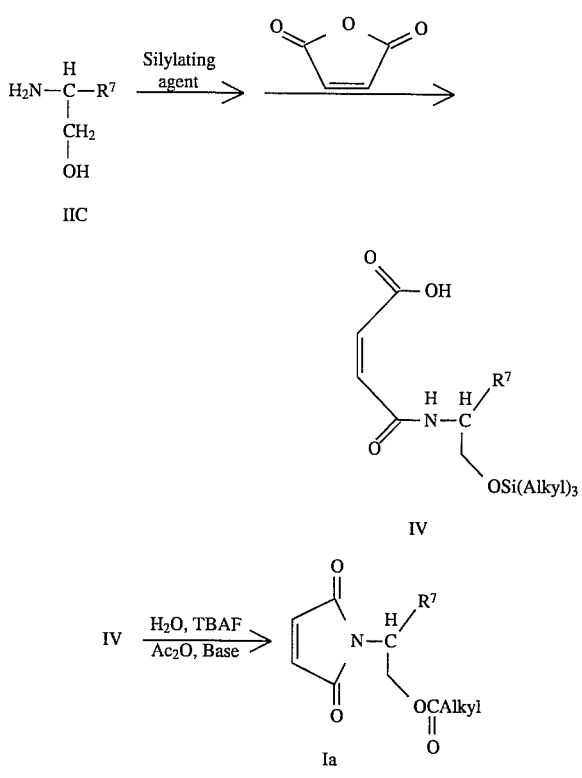

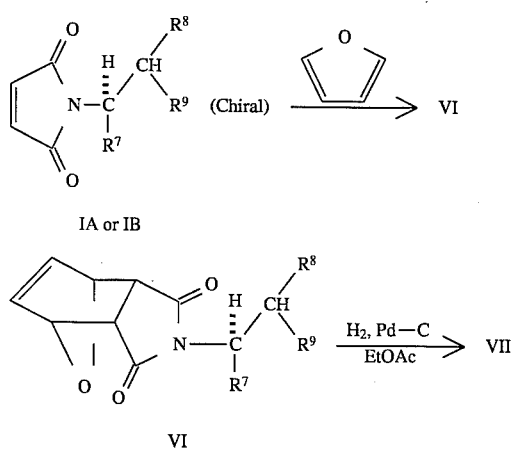

-continued
Reaction Scheme 3
Preparation of Thromboxane Receptor Antagonist V
Employing Maleimide Intermediate IA or IB (from Scheme 1)
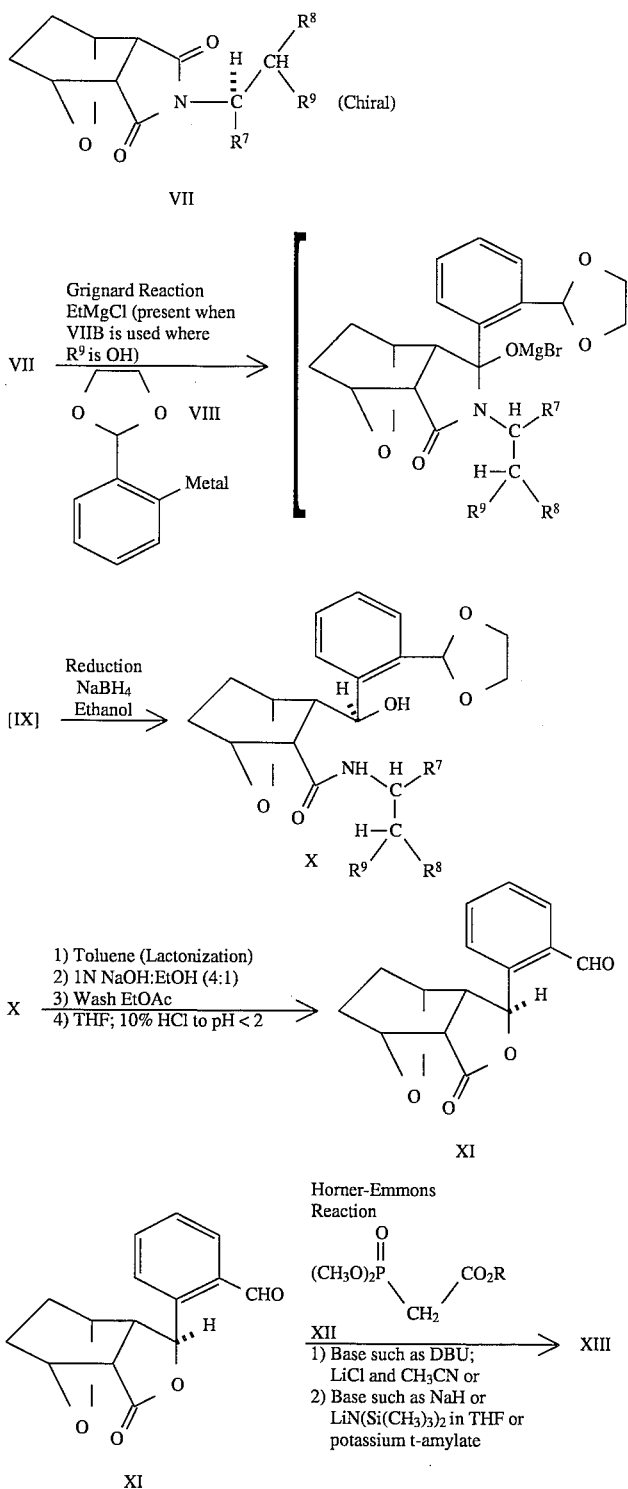

Reaction Scheme 3
Preparation of Thromboxane Receptor Antagonist V
Employing Maleimide Intermediate IA or IB (from Scheme 1)
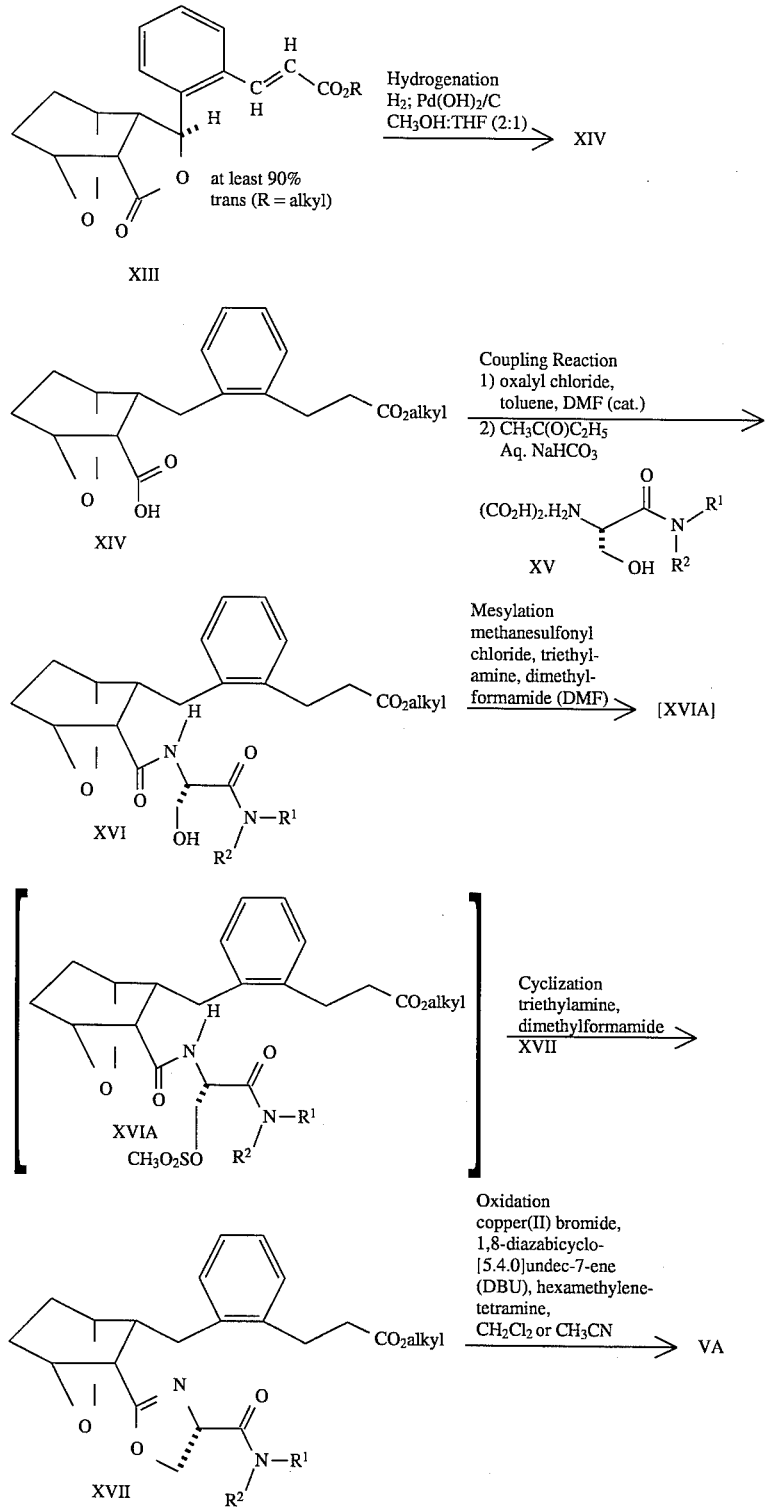

5,539,126

-continued
Reaction Scheme 3
Preparation of Thromboxane Receptor Antagonist V
Employing Maleimide Intermediate IA or IB (from Scheme 1)

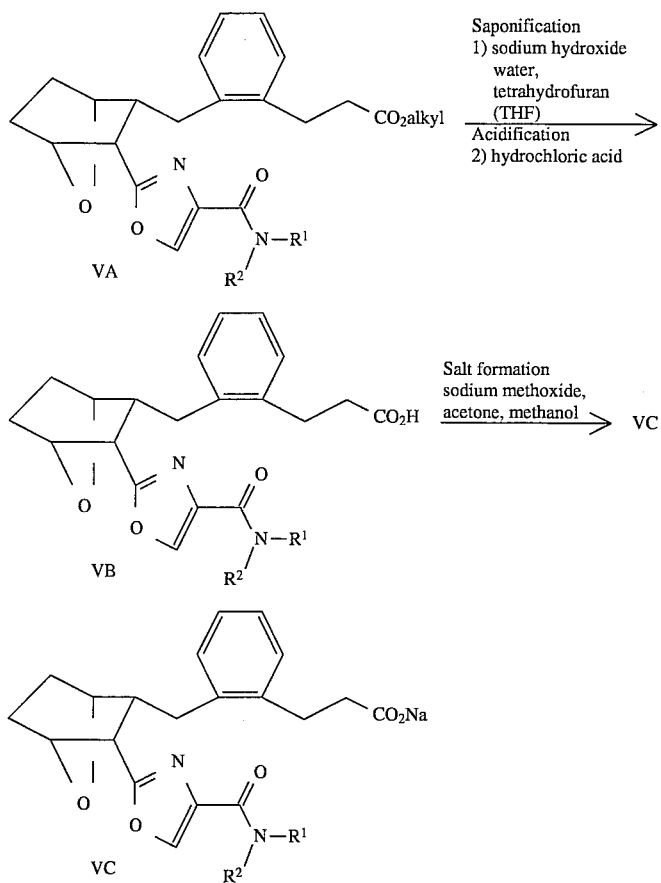

In addition, in accordance with the invention, a method for preparing thromboxane receptor antagonists VA, VB and VC is provided as shown in Reaction Scheme 3.

In Reaction Scheme 3, imide VII is prepared by a Diels-Alder reaction of maleimide IA or IB (which includes at least one chiral center) with furan employing a molar ratio of furan:IA or IB of within the range of from about 2.5:1 to about 10:1, preferably from about 3:1 to about 4:1, in the presence of a Lewis acid, such as $AlCl_3$, $AlBr_3$, $FeBr_3$, $TiCl_4$ or $SnCl_4$ and inert organic solvent such as methylene chloride, dichloroethane or toluene, under an inert atmosphere such as argon, to form the exo adduct VI. Exo adduct VI is reduced by reaction with hydrogen in the presence of a catalyst such as Pd/C, Pd-$BaSO_4$ or Pt—C, in the presence of inert organic solvent, such as ethyl acetate, toluene or tetrahydrofuran, to form imide VII.

Imide VII is then subjected to an addition reaction by treating VII with a metallated aryl compound of the structure

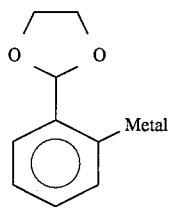

VIII wherein Metal is MgBr or Li. Where Metal is MgBr, such Grignard reagent VIII is prepared by dissolving the halide

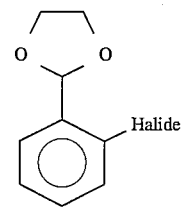

VIIIA (wherein halide refers to Br or I), in an inert organic solvent, such as THF, dioxane, toluene or t-butylmethyl ether, and mixing the so-formed solution with magnesium to give the aryl Grignard reagent VIII.

A cooled solution of imide VII in an inert organic solvent such as THF, t-butylmethyl ether, toluene or dioxane, is mixed with a solution of an alkyl (or aryl) magnesium halide such as ethylmagnesium chloride, ethylmagnesium bromide or phenylmagnesium chloride (used only if $R^9$ is OH) in the same solvent used for imide VII, followed by the Grignard reagent VIII, to form intermediate IX which is reduced, for example, by reaction with a reducing agent such as sodium borohydride, lithium borohydride or zinc borohydride, in the presence of an alcohol solvent such as ethanol or methanol, to form amide X.

Where the metallated aryl compound VIII to be employed is the aryl lithium derivative XB and $R_9$=OH, imide VII may be first treated with an alkyl lithium compound ($R^a$Li where $R^a$ is lower alkyl) such as methyllithium, ethyllithium or butyllithium, and then with the aryllithium derivative VIIIB

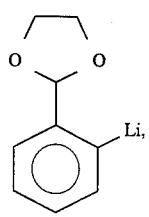
VIIIB in the presence of an inert organic solvent such as THF, toluene, tert-butylmethyl ether or diethyl ether. The resulting intermediate IXA (same as IX except MgBr is replaced with Li) is reduced as described for IX to form amide X.

Amide X is made to undergo lactonization by dissolving X in toluene and heating to form the lactone XA

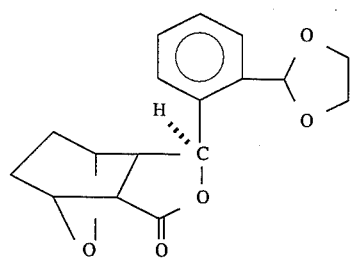
XA which is treated with water and a base such as NaOH, KOH, LiOH, Mg(OH)$_2$ or Ca(OH)$_2$ in the presence of an alcohol solvent such as ethanol or methanol, to form the salt XB

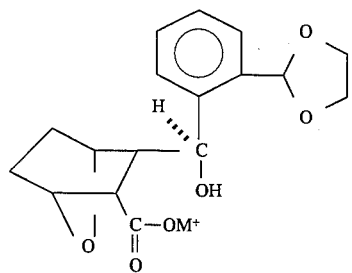
XB where M$^+$ is a metal ion such as Na$^+$, K$^+$ and the like.

X may be treated with NaOH directly to form salt XB.

Salt XB is then treated with strong acid such as hydrochloric acid, sulfuric acid, or nitric acid in the presence of an inert organic solvent, such as THF, isopropanol or dioxane, to form starting aldehyde XI as a single enantiomer as shown in Scheme 3.

Aldehyde XI, preferably in substantially enantiomerically pure form, is made to undergo a Horner-Emmons reaction wherein aldehyde XI is treated with a phosphonic diester compound XII in the presence of a base such as 1,8-diazabicyclo-[5.4.0]-undec-7-ene (DBU), or 1,5-diazabicyclo-[4.3.0]non-5-ene (DBN), or Hunig's base (diisopropylethylamine), preferably DBU, and an inert organic solvent such as acetonitrile, tetrahydrofuran (THF), dimethoxyethane or toluene, preferably, acetonitrile, and an alkali metal salt such as lithium chloride, lithium bromide, or an alkaline metal salt such as MgBr$_2$, or magnesium methoxide, to form the ester XIII wherein R is lower alkyl such as methyl or ethyl (ester XIII will be primarily in the form of the trans isomer).

Alternatively, the Horner-Emmons reaction may be carried out by substituting for DBU, as a base, an alkali metal hydride such as sodium hydride, or lithium bis(trimethylsilyl)amide, or potassium t-amylate, in an inert organic solvent such as tetrahydrofuran, toluene or dimethoxyethane.

In another variation, the aldehyde XI may be homologated to form ester XIV by treating XI with a magnesium salt of a monoalkyl malonate of the structure

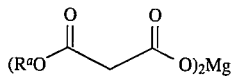
XIIA wherein R$^a$ is a lower alkyl, such as methyl or ethyl, in the presence of THF or other etheral solvent such as diethyl ether.

The ester XIII (primarily in the form of the trans isomer) will be subjected to a hydrogenation wherein ester XIII is treated with hydrogen in the presence of a hydrogenation catalyst such as Pd(OH)$_2$/C or Pd/C, and in the presence of an alcohol solvent such as methanol or ethanol, and an inert organic solvent such as THF, ethyl acetate or dioxane, to form carboxylic acid XIV.

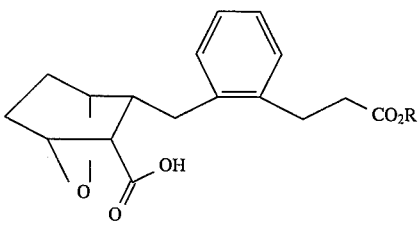
XIV wherein R is lower alkyl, preferably methyl or ethyl.

The carboxylic acid XIV intermediate is employed to prepare a thromboxane receptor antagonists VA-VC. Carboxylic acid XIV is subjected to a coupling reaction wherein carboxylic acid XIV in an inert solvent such as toluene, methylene chloride, or 1,2-dichloroethane is treated under an inert atmosphere with a catalytic amount of DMF. The resulting mixture is cooled below 0° C. and oxalyl chloride or other reagent for acid chloride formation such as thionyl chloride is added to form an acid chloride solution. Where thionyl chloride is to be employed, carboxylic acid XIV need not be treated with catalytic DMF.

Amide XV (prepared as described in Scheme 5) is added to an aqueous sodium bicarbonate solution and an inert organic solvent such as methyl ethyl ketone, methylene chloride or THF is added to form a biphasic mixture which is cooled to from about 30° to about −10° C. The previously prepared acid chloride solution is added and the mixture heated to a temperature within the range of from about 40° to about 80° C. to form amide XVI.

Amide XVI is mesylated by treating a solution of amide XVI in DMF or other solvent such as methylene chloride or THF, with an organic base such as triethylamine, pyridine or 2,6-lutidine and then while maintaining the mixture below about 5° C., methanesulfonyl chloride is added to form the mesylate XVIA. Mesylate XVIA is cyclized by treating XVIA with triethylamine or other organic base as set out above, in the presence of DMF or other solvent as set out above to form oxazoline XVII.

Oxazoline XVII is oxidized using cupric bromide and 1,8-diazabicyclo[5.4.0]undec-7-ene (DBU) in the presence of hexamethylenetetramine and inert organic solvent such as methylene chloride to form oxazole ester VA which is saponified by treatment with strong base such as NaOH, KOH and the like, in aqueous-organic solvent such as THF or dioxane, and then is acidified by treatment with strong acid such as HCl, sulfuric acid or trifluoroacetic acid to form oxazole acid VB. Oxazole acid VB may then be treated with alkali metal alkoxide such as sodium methoxide, sodium 2-ethyl-hexanoate or sodium ethoxide, in the presence of inert organic solvent such as acetone, THF or ethyl acetate, and an alcohol such as methanol or ethanol to form oxazole salt VC.

Referring to Reaction Scheme 5, the amide XV (used in Scheme 3) is prepared by reacting an aqueous solution of L-serine and NaOH with benzyl chloroformate to form carbobenzyloxy-L-serine which is treated with DBU under an inert atmosphere. Thereafter trimethylacetyl chloride and amine XX are added to form amide XXI which is deprotected by treatment with $H_2$ and Pd/C in the presence of an alcohol solvent, such as ethanol or methanol, to form amide XXII which is treated with oxalic acid (or another acid such as $HC_1$ or trifluoroacetic acid) in the presence of alcohol solvent such as ethanol or methanol to form amide XV.

In the amine XX, $R^1$ and $R^2$ are as defined in U.S. Pat. No. 5,100,889 which is incorporated herein by reference.

Thus $R^1$ is hydrogen, lower alkyl, aralkyl, aryl, cycloalkyl, cycloalkylalkyl, or amide.

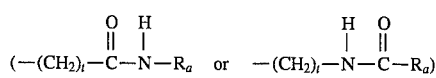

wherein t is 1 to 12 and $R_a$ is lower alkyl, aryl, cycloalkyl, or cycloalkylalkyl); and $R^2$ is hydrogen, lower alkyl, aryl, or aralkyl; or $R^1$ and $R^2$ together with the nitrogen to which they are linked may form a 5- to 8-membered ring.

$R^1$ is preferably lower alkyl such as n-pentyl, aryl such as phenyl, halophenyl such as 4-chlorophenyl, or cyclohexylalkyl, such as cyclohexylbutyl.

$R^2$ is preferably H or phenyl.

Reaction Scheme 4
Preparation of Thromboxane Receptor Antagonist I
Employing Maleimide Intermediate Ia (from Scheme 2)

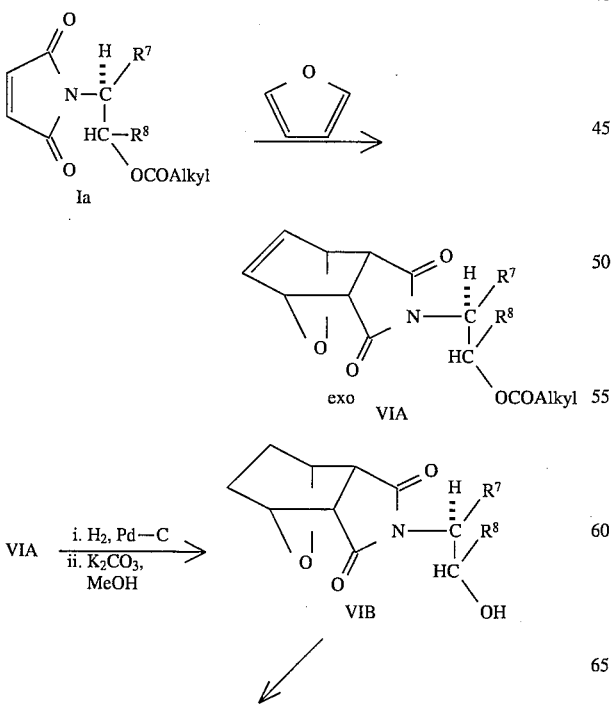

-continued
Reaction Scheme 4
Preparation of Thromboxane Receptor Antagonist I
Employing Maleimide Intermediate Ia (from Scheme 2)

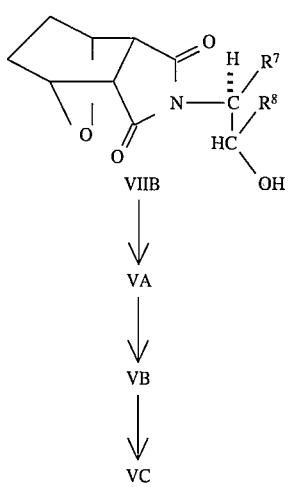

Still further in accordance with the present invention, a method for preparing thromboxane receptor antagonists VA, VB and VC is provided as shown in Reaction Scheme 4.

Compound Ia is reacted with furan (employing a ratio of furan:Ia of within the range of from about 0 30:1 to about 15:1, preferably from about 25:1 to about 20:1, in the presence of a Lewis acid catalyst, such as $SnCl_4$, $AlCl_3$, $AlBr_3$, $FeBr_3$, $ZnI_2$ or $TiCl_4$, in an inert organic solvent such as dichloromethane, dichloroethane or toluene to form exo compound VIA.

Compound VIA is reacted with hydrogen in the presence of a catalyst such as Pd/C, Pd-$BaSO_4$ or Pt—C, to form VIB, followed by deacetylation with alkali metal carbonate, such as $K_2CO_3$ or $Li_2CO_3$ or $Na_2CO_3$, preferably $K_2CO_3$ to form VIIB.

Imide VIIB may then be employed in place of imide VII to prepare compounds of formulae VA, VB and VC following Reaction Scheme 3.

Reaction Scheme 5
Preparation of Starting Compound XV

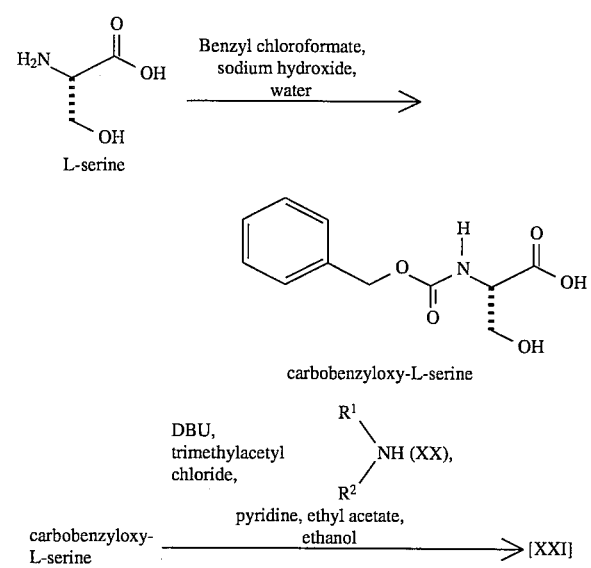

-continued
Reaction Scheme 5
Preparation of Starting Compound XV

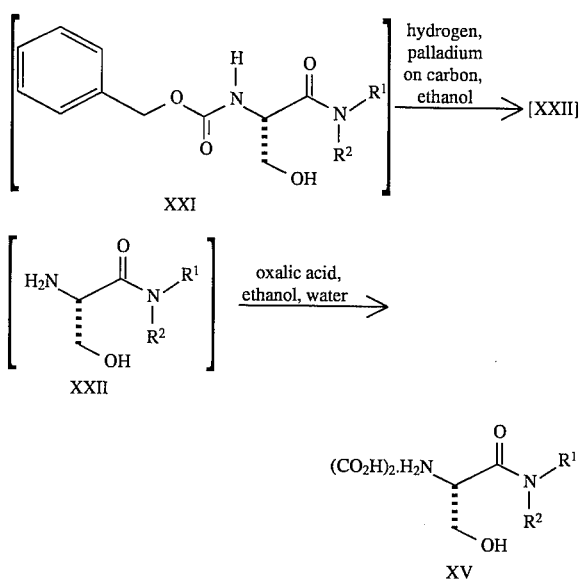

DETAILED DESCRIPTION OF THE INVENTION

In carrying out the method of the invention as shown in Scheme 3, the Horner-Emmons reaction for preparing carboxylic acid XIV, is carried out in the presence of base and optionally an alkali or alkaline earth metal salt such as a lithium halide, for example, lithium chloride, lithium bromide, lithium iodide or magnesium bromide, employing a molar ratio of phosphonic acid XII:aldehyde XI of within the range of from about 1:1 to about 1.5:1, preferably from about 1:1 to about 1.2:1, under an inert atmosphere such as argon or nitrogen, to form the ester XIII in a ratio of trans:cis isomers of within the range of from about 14:1 to about 36:1.

Where ester XIII is formed by homologation of aldehyde XI employing the magnesium salt of a monoalkylmalonate (XIIA), the magnesium salt XIIA will be employed in a molar ratio to aldehyde XI of within the range of from about 1:1 to about 2:1.

The so-formed ester XIII is then hydrogenated preferably employing Pearlman's catalyst (Pd(OH)$_2$/C) to form the carboxylic acid XIV. Other catalysts, such as palladium on carbon may be employed in carrying out the hydrogenation step.

The imide VII is subjected to an addition reaction, such as a Grignard reaction, to ultimately form aldehyde XI of desired optical purity.

In carrying out the Grignard reaction, the aryl Grignard reagent VIII is prepared by treating a solution of 2-(2-halophenyl)-1,3-dioxolane (where halo is Br or I) in THF or other inert organic solvent such as dioxane or t-butylmethyl ether, with magnesium, preferably in the form of Mg turnings, employing a molar ratio of Mg:2-(2-bromophenyl)-1,3-dioxolane of within the range of from about 2:1 to about 1.0:1, preferably from about 1.1:1 to about 1.5:1.

If imide VIIB is used, instead of VIIA, which has $R_9$=OH, then imide VIIB is first treated with an alkyl- or aryl- magnesium halide (e.g. Cl$^-$, Br$^-$ or I$^-$), preferably ethyl magnesium chloride, employing a molar ratio of imide VIIB to ethylmagnesium halide within the range of from about 1:1.1 to 1:1. The aryl Grignard reagent VIII (made as described above) is then mixed with the reaction solution employing a molar ratio of imide VII to aryl Grignard reagent VIII of within the range of from about 1:4 to about 1:1, preferably from about 1:1.2 to about 1:2.5. If imide VIIA is used then the aryl Grignard reagent VIII (made as described above) is mixed with imide VIIA employing a molar ratio of imide VIIA to aryl Grignard reagent VIII of within the range of from about 1:3 to about 1:1.1, preferably from about 1.4 to about 1:2.

To achieve desired optical purity in the final aldehyde XI, it is preferred that the Grignard reaction be carried out employing ethylmagnesium chloride in a molar ratio to imide VIIB of within the range of from about 0.9:1 to about 1.2:1, preferably from about 1.0:1 to about 1.1:1. The ethylmagnesium chloride will be employed in solution, preferably in THF, at a concentration of within the range of from about 1.0M to about 2.5M, preferably from about about 1.5M to about 2.0M. The reaction of VIII with imide VIIB will be carried out at a temperature within the range of from about –78° C. to about 40° C., preferably from about –40° to about 20° C.

The ratio of desired to undesired enantiomers obtained using the above conditions will range from about 90:10 to >99:1.

Ethylmagnesium bromide may be employed in place of ethylmagnesium chloride with a resulting decrease in ratio of desired to undesired enantiomers for imides VIIB where $R_9$=OH.

Where the addition reaction of imide VIIB having $R_9$=OH to form intermediate IX is carried out employing the metallated aryl compound VIII where the metal is Li, imide VIIB is first treated with the alkyl lithium compound $R^a$Li employing a molar ratio of $R^a$Li:VIIB of within the range of from about 0.9:1 to about 1.2:1. The imide VIIB is then treated with the Li aryl compound VIIIB employing a molar ratio of VIIIB:VIIB of within the range of from about 1:1 to about 1:3.

The above reactions are carried out at a temperature within the range of from about –78° C. to about 40° C.

The alcoholate IX resulting from the addition reaction, such as the Grignard reaction is then reduced employing a molar ratio of reducing agent:IX of within the range of from about 0.5:1 to about 3:1, preferably from about 0.8:1 to about 2:1.

The resulting amide X is made to undergo lactonization employing a molar ratio of toluene:X of within the range of from about 20:1 to about 10:1, preferably from about 16:1 to about 12:1. The toluene-X mixture is heated to a temperature of within the range of form about 60° to about 120° C., preferably from about 110° to about 115° C. to form lactone XA. Lactone XA is treated with base:alcohol in a molar ratio of within the range of from about 0.1:1 to about 1.0:1, preferably from about 0.2:1 to about 0.4:1. The mixture is extracted with ethyl acetate and the aqueous layer is acidified with strong acid to achieve a pH of within the range of from about 1 to about 2.

The ethyl acetate wash may be treated with an acid such as oxalic acid and used to recrystallize starting material IIC ($R^7$=C$_6$H$_5$) such as (S)-phenylglycinol•(CO$_2$H)$_2$.

The halide compound

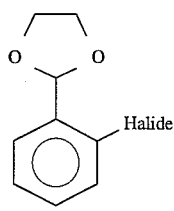

(for example, 2-(2-bromophenyl)-1,3-dioxolane) employed to prepare Grignard reagent VIII is prepared by reaction of the aldehyde

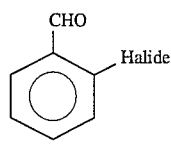

with ethylene glycol and p-toluenesulfonic acid in the presence of an aromatic solvent such as toluene, benzene or xylene, under an inert atmosphere such as nitrogen, at a temperature within the range of from about 80° to about 150° C., preferably at reflux.

In carrying out the preparation of the thromboxane receptor antagonist products VB and VC, amide XV is employed in a molar ratio to acid XIV of within the range of from about 1.5:1 to about 1:1, preferably from about 1.1:1 to about 1:1, to form amide XVI. Amide XVI is mesylated employing a molar ratio of methanesulfonyl chloride:XVI of within the range of from about 2:1 to about 1:1, preferably from about 1.3:1 to about 1:1 and a temperature within the range of from about −20° to about 60° C., preferably from about 0° to about 25° C.

The resulting mesylate XVIA is cyclized employing a molar ratio of triethylamine or other organic base:XVIA of within the range of from about 4:1 to about 2:1, preferably from about 3.5:1 to about 2.5:1, to form oxazoline XVII. Other organic bases which may be employed include diisopropylethylamine, pyridine or 2,6-lutidine.

The cupric bromide oxidation of oxazoline XVII is carried out at a temperature of within the range of from about 20° C. to about 70° C., employing a molar ratio of cupric bromide to oxazoline XVII of within the range of from about 2:1 to about 6:1 and a molar ratio of cupric bromide to DBU of within the range of from about 1:1 to about 1:3 in an inert solvent, preferably methylene chloride. The oxidation is preferably carried out in the presence of a base such as hexamethylenetetramine which is disclosed in U.S. Pat. No. 5,281,716, which is incorporated herein by reference.

The so-formed oxazole ester VA may then be hydrolyzed employing conventional techniques such as by treatment with an aqueous solution of alkali metal base and then aqueous acid to form the corresponding acid VB which may be treated with sodium methoxide, sodium 2-ethylhexanoate or sodium ethoxide to form salt VC in the presence of acetone/methanol.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 substituents such as halo, alkenyl, alkynyl, aryl, alkyl-aryl, haloaryl, cycloalkyl, or alkylcycloalkyl.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, and/or alkoxy groups.

The term "aryl" or "Ar" as employed herein refers to monocyclic or bicyclic aromatic groups containing from 6 to 10 carbons in the ring portion, such as phenyl or naphthyl. Aryl (or Ar), phenyl or naphthyl may include substituted aryl, substituted phenyl or substituted naphthyl, which may include 1 or 2 substituents on either the phenyl or naphthyl such as lower alkyl,trifluoromethyl, halogen (Cl, Br, I or F), alkylsulfonyl, and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to Cl, Br, F or I, with Cl preferred.

The final compounds IB and IC prepared by the method of this invention are thromboxane receptor antagonists and as such are useful as inhibitors of thromboxane receptor mediated actions. The term "thromboxane receptor antagonist" includes compounds which are so-called thromboxane $A^2$ receptor antagonists, thromboxane $A^2$ antagonists, thromboxane $A_2$/prostaglandin endoperoxide antagonists, TP-receptor antagonists, or thromboxane antagonists.

The compounds prepared by the method of the invention are also thromboxane synthetase inhibitors and thus are useful as inhibitors of thromboxane production.

Examples of various utilities of the compounds prepared by the method of the invention are set out in U.S. Pat. No. 5,100,889.

The following Examples represent preferred embodiments of the present invention. Unless otherwise indicated, all temperatures are expressed in degrees Centigrade.

EXAMPLE 1

(S)-1-[2-(Acetyloxy)-1-phenylethyl]-2,5-dihydro-1H-pyrrol- 2,5-dione

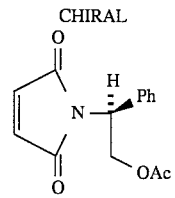

1,3-Bis(trimethylsilyl)urea (0.745 g, 3.65 mM) was added to (S)-(+)-2-phenylglycinol (0.5 g, 3.65 mM) dissolved in THF (10 ml, distilled from Na/benzophenone). The mixture was refluxed for 1 hr. A precipitate formed. Maleic anhydride (0.376 g, 3.83 mM) was added and the mixture refluxed for 0.5 hr. $H_2O$ (66 µl, 3.65 mM) was added to the cooled mixture and stirred for 30 min. to form the intermediate

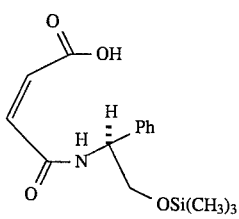

which was not recovered from the reaction mixture. Tetrabutyl-ammonium fluoride (TBAF•3H₂O, 0.115 g, 0.365 mM), acetic anhydride (AC₂O) (3.44 ml, 36.5 mM), and triethylamine (TEA) (3.0 ml, 21.9 mM) were added and the mixture refluxed for 2.5 hrs. After cooling to room temperature, H₂O (15 ml) was added and stirred for 1 hr. The reaction mixture was taken up in EtOAc (75 ml), washed with water (2×50 ml), 5% NaHCO₃ (50 ml), brine (25 ml), dried (MgSO₄), and evaporated to a black oil: 0.88 g. The oil was Kugalrohr distilled under vacuum (~0.3 mm), oven temperature 110°–30°, giving title compound as a colorless oil: 0.79 g (83% yield). TLC (silica gel, EtOAc/hexane 7:3 visualized with UV and KMnO₄) showed the product as one spot at Rf 0.60.

Calcd. for C₁₄H₁₃NO₄ (259.26) C, 64.86; H, 5.05; N, 5.40 Found: C, 65.15; H, 5.05; N, 5.31; H₂O 0.00 (KF)

EXAMPLE 2

[2S-(2-(2α,3aα,4β,7β,7aα)]-2-(Octahydro-3-oxo-4, 7-epoxyisobenzofuran- 1-yl) benzaldehyde A. [2(S),3aα,4β,7β,7aα]-2-[2-(Acetyloxy)-1-phenylethyl]-3a,4,7,7a-tetrahydro-4,7-epoxy-1H-isoindole-1, 3(2H)dione

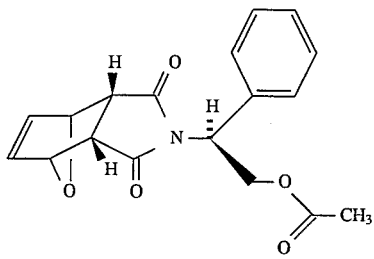

Tin chloride (2.90 ml, 2.90 mM, 1.0M in CH₂Cl₂) was added by syringe to 10 ml CH₂Cl₂ at room temperature under argon. Example 1 compound (0.5 g, 1.93 mM) in 1 ml CH₂Cl₂ was added and then furan (0.70 ml, 9.65 mM) was introduced. After 6 hours another 0.70 ml furan was added and the mixture stirred overnight. The mixture turned brown and a precipitate formed. The mixture was taken up in EtOAc (75 ml)/1N HCl (25 ml). It was filtered to remove the brown insoluble material. The layers were separated, and the EtOAc layer was washed with 1N HCl (25 ml), water (25 ml), 5% NaHCO₃ (25 ml), brine (10 ml), dried (MgSO₄), and evaporated to a yellow foam: 0.681 g.

The foam was taken up in 30 ml warm MeOH, stirred with 5 g charcoal for 15 min, filtered through Celite, and evaporated to a slightly colored oil: 0.55 g. The oil was triturated with 3 ml MeOH. Crystals formed immediately. After standing at 0° for 1 hour, the crystals were filtered, washed with cold MeOH (2×1 ml) and dried under vacuum overnight to give title compound: 0.47 g (75%), mp. 117°–9°, [α]_D +14.5° (c=1, CHCl₃).

Anal. calcd. for C₁₈H₁₇NO₅•0.1 H₂O (MW 327.32/329.2) C, 65.67; H, 5.27; N, 4.25; H₂O 0.57 Found: C, 65.75; H, 5.07; N, 4.43; H₂O 0.57 (KF)

B. [2(S),3aα,4β,7β,7aα]-Hexahydro-2-(2-hydroxy-1-phenylethyl)-4,7-epoxy-1H-isoindole1,3(2H)-dione

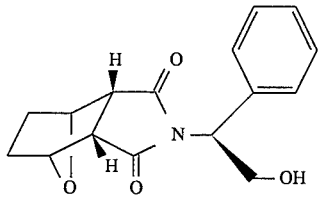

Part A compound (0.400 g, 1.22 mM) and 5% Pd/C (40 mg) were stirred in EtOAc (10 ml) and H₂ was sparged through the mixture for 1.2 hrs. TLC (silica gel, EtOAc/hexane 7:3 visualized with UV and KMnO₄) showed the Part B olefin and the saturated intermediate

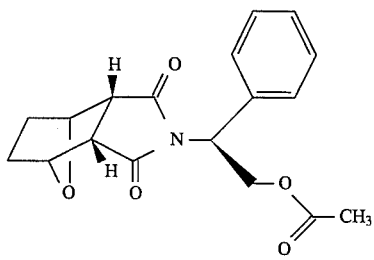

with the same Rf 0.44. The olefin spot was KMnO₄ positive while the spot for the saturated intermediate (UV positive) from the reaction mixture was negative. N₂ was sparged through the mixture for 15 min to remove excess H₂. The catalyst was filtered through Celite and washed with EtOAc (4×2 ml). The filtrate was evaporated to an oil which solidified on standing after 2 days to saturated intermediate as fine white needles: 415 mg (quan. yield), mp. 96°–8°.

The above solid saturated intermediate (0.360 g, 1.06 mM) was dissolved in MeOH (10 ml) and K₂CO₃ (15 mg) was added and stirred for 4 hrs. The K₂CO₃ gradually dissolved. TLC (silica gel, EtOAc/hexane 7:3, visualized with UV and ceric ammonium molybdate) showed disappearance of saturated intermediate and appearance of a spot for the title compound at R_f 0.20. MeOH was evaporated and the residue was taken up in EtOAc (25 ml) and washed with 1N HCl (10 ml), H₂O (10 ml), 5% NaHCO₃ (10 ml), and brine (10 ml), dried (MgSO₄), and evaporated: 0.29 g.

The residue was dissolved in hot EtOAc (1.5 ml) and hexane (3 ml) was added with heating. The solution was let stand at room temperature for 3 hrs and at 0° for 2 hrs. The crystals were filtered, washed with cold hexane, and dried under vacuum overnight to give title compound as a white solid: 0.25 g (82%), mp 118°–9°, [α]_D −16.0° (c=1.3, CHCl₃).

Anal. calcd. for C₁₆H₁₇NO₄, (MW 287.1) C, 66.89; H, 5.96; N, 4.88 Found: C, 66.83; H, 6.01; N, 5.06; H₂O 0.00 (KF)

C. 2-(2-Bromophenyl)-1,3-dioxolane

A 12 L 3-necked flask fitted with an overhead stirrer was charged with 2-bromobenzaldehyde (800 g, 4.324 moles), ethylene glycol (402.6 g, 6.485 moles), p-toluenesulfonic acid•H₂O (3.95 g, 0.021 moles) and toluene (3.785 kg, 41.074 moles).

One side of the flask was stoppered (glass) and a Dean-Stark separator/condenser/N₂ port was attached to the other side.

The heterogeneous yellow reaction mixture was stirred under a nitrogen atmosphere and heated to reflux for about 45 minutes.

Water was collected via the Dean-Stark separator and the residue was cooled to room temperature, washed with 1.2 L of saturated aqueous NaHCO$_3$ followed by 1.2 L of saturated aqueous NaCl.

The combined organic layers were dried over anhydrous MgSO$_4$, filtered, concentrated on a rotary evaporator and dried under high vacuum to provide title compound in the form of an oil. The so-formed oil was vacuum distilled to provide 52 g and 876.2 g of title compound (88.9% yield).

D. [2S-(2α,3aα,4β,7β,7aα)]-2-(Octahydro-3-oxo-4,7-epoxyisobenzofuran-1-yl)benzaldehyde Into an oven-dried, argon purged 500 ml flask, Part C 2-(2-bromophenyl)-1,3-dioxolane (71.5 g, 0.313 mol) was dissolved in THF (240 ml). Magnesium turnings (11.4 g, 0.467 mol) were charged into a separate oven-dried, argon-purged 500 ml 3-necked flask equipped with a condenser. To this flask was added a portion (10.0 ml) of the above solution at room temperature. The reaction initiated by itself after stirring for 5 min. The rest of the solution was added into the flask at such a rate which maintained a gentle reflux. After all of the solution had been added, the reaction mixture was stirred for an additional 2.0 h at room temperature to give the aryl Grignard reagent bromo[2-(1,3-dioxolan-2-yl)phenyl] magnesium.

The Part B imide (50.0 g, which included 2 g from a previous batch, 0.174 mol) was added to an oven-dried, argon purged 3.0 L 3-necked flask equipped with an addition funnel, dissolved in THF (790 ml), and cooled to −15 ° C. in an ice-methanol bath. To this solution was added C$_2$H$_5$MgCl (87.0 ml of a 2.0M solution in THF) dropwise over a period of 0.5 hour via the addition funnel. After the addition was complete, the reaction was stirred for 0.5 hour at −15° C. The ice-methanol bath was removed and replaced with an ice-water bath. The reaction mixture was stirred for an additional 0.5 hour at 0° C. To this mixture was added dropwise over a period of 1.0 hour the above aryl Grignard solution (280 ml of a 1.12M solution in THF, 0.313 mol). After the addition was complete, the reaction was stirred at 0° C. for 3.0 h. The ice-water bath was removed and the reaction was stirred for an additional 4.5 h. The reaction mixture was cooled to 0° C. with an ice-water bath and quenched by adding ethanol (1.0 L).

To the resulting mixture was added solid NaBH$_4$ (15.0 g, 0.397 mol) in 6 equal portions over 0.5 hour. The ice-water bath was allowed to melt and the reaction mixture was allowed to warm to room temperature and stirred for 14 h. The reaction mixture was poured into 10% Na$_2$CO$_3$ (1.5 L) and the mixture was extracted with ethyl acetate (3×1.5 L). The organic extracts were combined, washed with brine (1.5 L), dried over MgSO$_4$, filtered and concentrated in vacuo on the rotary evaporator as described above to obtain the crude [1R-[1α,2α(S*),3aα,4α]-3-[[2-(1,3-dioxolan-2-yl)phenyl] hydroxymethyl]-N-(2-hydroxy-1-phenylethyl)-7-oxabicyclo[2.2.1]heptane-2-carboxamide (104.0 g, 110%) which was used in the next step without any additional purification.

The above crude alcohol (104.0 g) was dissolved in toluene (250 ml) and heated to reflux for 3.0 h. The resulting solution was cooled to room temperature and then 1N NaOH (750 ml) and ethanol (150 ml) were added. The mixture was vigorously stirred for 4.0 h at room temperature and then was extracted with ethyl acetate (750 ml). The aqueous layer was mixed with THF (125 ml). To this mixture was added 10% HCl (350 ml) at room temperature. The resulting mixture was then stirred at room temperature for 14 h during which time a white precipitate formed. The reaction was cooled to 0° C. for 1.0 hour. The white precipitate was filtered off using a medium fritted glass filter and washed with water (100 ml). The solid was dried under high vacuum to give title compound as a white solid (32.0 g, 71%) with 99.9% ee as determined by chiral HPLC.

EXAMPLE 3

[1S-(1α,2α,3α,4α)-2-[[2-(3-Methoxy-3-oxopropyl)phenyl]methyl]-7-oxabicyclo[2.2.1]heptane-3 -carboxylic acid A. [1S-[1α(E),3aα,4β,7β,7aα]]-3-[2-(Octahydro-3-oxo-4,7-epoxyisobenzofuran-1 -yl)phenyl]-2-propenoic acid, methyl ester In a 250 mL flask was placed Example 2 aldehyde (obtained from two different batches) (9.44 g, 36.54 mmole), lithium chloride (1.7 g, 40.19 mmole) and acetonitrile (145 mL). The solution was stirred magnetically under an argon atmosphere. Trimethylphosphonoacetate (7.32 g, 40.19 mmole) was added via syringe followed by 1,8-diazabicyclo [5.4.0]undec-7-ene (DBU) (6.01 mL, 40.19 mmole). The solution became cloudy and the temperature of the reaction rose to 42° C. After 75 minutes, TLC indicated the reaction to be complete. The mixture was poured into aqueous saturated sodium bicarbonate (500 mL) and extracted with methylene chloride (2×500 mL). The combined organic layers were dried over anhydrous magnesium sulfate, filtered, concentrated on a rotary evaporator (bath temp. 35° C., ~80mm Hg) and dried under high vacuum (~0.5 mm Hg) at room temperature to provide 11.36 g (98.9% yield) of crude title compound as a yellow, crystalline solid.

B. [1S-(1α,2α,3α,4α)]-2-[[2-Methoxy-3-oxopropyl)phenyl]methyl]-7-oxabicyclo[2.2.1]heptane-3-carboxylic acid The Part A crude unsaturated ester (11.36 g) was placed in a 250 mL flask and dissolved in THF (35 mL) and methanol (70 mL). To the magnetically stirred solution was added Pearlman's catalyst (Aldrich) (Pd(OH)$_2$/C) (1.14 g). The flask was evacuated, then connected to a balloon filled with hydrogen. After being stirred at room temperature for 2 hours, a second portion of Pearlman's catalyst (1.14 g) was added. The flask was re-evacuated and reconnected to the balloon filled with hydrogen. The mixture was stirred at room temperature for an additional 2 hours. TLC indicated complete conversion to title compound. The balloon was removed and celite (2.0 g) was added to the mixture and stirred for 10 minutes. The mixture was filtered through a pad of Celite (45×25mm). The pad was washed with methanol (50 mL). The filtrate was concentrated on a rotary evaporator as described above to provide a yellow oil. The oil was dissolved in methylene chloride (100 mL) and dried over anhydrous magnesium sulfate. The solution was filtered, concentrated on a rotary evaporator as described above, and dried under high vacuum (~0.5 mm Hg) to provide 11.81 g (101.6% yield) of crude title compound.

The above crude title compound (11.81 g) was dissolved in hot ethyl acetate (23 mL) and diluted with hot heptane (46 mL). The mixture was allowed to cool while being stirred magnetically. The mixture was seeded at a temperature of 58° C. with crystals of title compound. Upon cooling to room temperature, a significant quantity of title compound had crystallized from the solution. An additional portion of heptane (65 mL) was added and the mixture was stirred for 5 minutes. The mixture was allowed to stand at room temperature overnight. The resulting solid was collected by suction filtration, washed with heptane (50 mL), then dried under high vacuum at room temperature to provide 7.32 g (62.9% yield) of title compound containing small traces of yellow material.

The solid and the mother liquor were recombined and dissolved in ethyl acetate (120 mL) and treated with Darco KB activated carbon (1.2 g). The mixture was heated to reflux for 2 minutes, then allowed to cool to room temperature. Celite (2.4 g) was added, and the mixture was stirred for 10 minutes, then filtered through a pad of Celite (45×25 mm). The pad was washed with ethyl acetate (50 mL). The filtrates were concentrated on a rotary evaporator as described above to provide a pale yellow oil. The oil was dissolved in ethyl acetate (23 mL), heated to reflux and diluted with heptane (46 mL). The mixture was then allowed to cool to room temperature with stirring. The mixture was seeded with crystals of title compound. After stirring at room temperature for ~15 minutes, additional heptane (65 mL) was added. The flask was placed in a cold room (~4° C.) overnight. The resulting crystals were collected by suction filtration, washed with heptane (50 mL) and dried under high vacuum (~0.5 mm Hg) at room temperature to provide 9.97 g (85.7% yield) of title compound.

EXAMPLE 4

N-Pentyl-L-Serinamide

A. Carbobenzyloxy-L-serine

L-Serine (20.00 g, 190.3 mmol) was dissolved in water, and aqueous sodium hydroxide was added to adjust the pH of the solution to about 8.5 while maintaining the temperature at about 25° C. Benzyl chloroformate (36.0 g, 211.0 mmol) was added while the pH was maintained between 8.3 and 8.5 by the addition of aqueous sodium hydroxide and the temperature was maintained at about 30° C. The mixture was stirred for about 2 hours. The reaction mixture was extracted with methylene chloride. The phases were separated, and the pH of the aqueous phase was adjusted to about 7 with concentrated hydrochloric acid. The aqueous phase was heated to about 40° C. under low vacuum to remove any residual methylene chloride. Water was added and the aqueous solution was heated to about 60° C. The pH was adjusted to about 2 with concentrated hydrochloric acid while maintaining the temperature at about 60° C. The solution was cooled to about 50° C. while stirring and seed crystals were added. With stirring, cooling was continued to about 0° C. to complete the crystallization. The product was collected and the cake was washed with cold (about 5° C.) water. The product was dried under vacuum at about 40° C. to afford carbobenzyloxy-L-serine.

B. N-Pentyl-L-serinamide, oxalate (1:1) salt

Under an inert atmosphere, 1,8-diazabicyclo[5.4.0]undec-7-ene (5.10 g, 33.5 mmol) was added to a suspension of Part A carbobenzyloxy-L-serine (7.50 g, 1.4 mmol) in ethanol. Ethyl acetate was added and the mixture was agitated (optionally, with heating up to about 50° C.) to obtain a clear solution. Pyridine (0.25 g, 3.2 mmol) was added and the mixture was cooled to about −30° C. Trimethylacetyl chloride (4.12 g, 34.2 mmol) was added and the mixture was maintained at about −30° C. With cooling, n-amylamine (3.00 g, 34.4 mmol) was added and the mixture was stirred at about −10° C. for about 2 hours. Cooling was discontinued and aqueous phosphoric acid was added. The mixture was warmed to about 10° C. and the phases were separated. The organic solution was washed sequentially with aqueous phosphoric acid, aqueous potassium carbonate, and brine. Throughout these extractions, the aqueous phase was back extracted with ethyl acetate. The combined organic solution was distilled under vacuum at about 25° C. while ethanol was added until all of the ethyl acetate was removed. Under an inert atmosphere, 10% palladium on carbon (50% water, 0.75 g) was added. The resulting mixture was purged with nitrogen and then stirred in the presence of hydrogen at about 25° C. for about 6 hours. The catalyst was removed by filtration, and the clear filtrate was partially concentrated under vacuum at about 30° C. The concentrated filtrate was added to a solution of oxalic acid dihydrate (4.35 g, 34.5 mmol) in ethanol and water and a thick precipitate was formed. The suspension was heated to reflux to obtain a clear solution. Water was added at the reflux temperature until a slight turbidity was observed. The mixture was cooled to about 0° C. and stirred until crystallization was complete (about 1 hour). The product was collected and the cake was washed with ethanol. The product was dried under vacuum at about 25° C. to afford title compound.

EXAMPLE 5

[1S-(1α,2α,3α,4α)]-2-[[3-[4-[(Pentylamino) carbonyl]-2-oxazolyl]-7-oxabicyclo[2.2.1] hept-2-yl]methyl]benzenepropanoic acid, monosodium salt A. [1S-[1α,2α,3α(R*),4α]]-2-[[3-[[[1-(Hydroxymethyl)-2-oxo-2-(pentylamino)ethyl]amino]carbonyl]-7-oxabicyclo [2.2.1]-hept-2-yl]methyl]benzenepropanoic acid, methyl ester Under an inert atmosphere, a catalytic amount of dimethylformamide (0,067 mL, 0.87 mmol) was added to a solution of Example 3 carboxylic acid (6.66 g, 20.9 mmol) in toluene and the resulting mixture was cooled to about 0° C. While maintaining the temperature below 0° C., oxalyl chloride (2.96 g, 23.3 mmol) was added and the mixture was stirred at about 5° C. for about 3 hours. The resulting acid chloride solution was partially concentrated under vacuum at about 40° C. and then used in the coupling reaction described below.

Meanwhile, Example 4 amide (6.17 g, 23.3 mmol) was added to a solution of sodium bicarbonate (9.63 g, 115 mmol) in water while the temperature was maintained at about 20° C. Methyl ethyl ketone was added and the biphasic mixture was cooled to about 0° C. While maintaining the temperature at about 0° C., the previously prepared acid chloride solution was added with stirring. The mixture was stirred at about 5° C. for about 20 hours and then heated to about 60° C. and the phases were allowed to separate. The organic phase was washed at about 50° C. sequentially with saturated sodium bicarbonate solution, aqueous phosphoric acid, and brine. The organic solution was partially concentrated under vacuum at about 40° C. to obtain a thick suspension. n-Heptane was added and the resulting mixture was cooled to about 20° C. with stirring. The product was collected and the cake was washed with n-heptane. The product was dried under vacuum at about 35° C. to afford title ester.

B. [1S-[1α,2α,3α(R*),4α]]-2-[[3-[4,5-Dihydro-4-[(Pentylamino)carbonyl]-2-oxazolyl]-7-oxabicyclo[2.2.1]hept-2-yl]methyl]benzenepropanoic acid, methyl ester Under an inert atmosphere, Part A ester (7.00 g, 14.7 mmol) was dissolved in dry dimethylformamide. The moisture content of the resulting solution must be <0.1% w/w; if it was higher, the solution was first dried by vacuum distillation of a portion of the solvent and dry dimethylformamide was added to restore the original solution volume. Triethylamine (4.29 g, 42.4 mmol, plus approximately 1 mmol per mmol of water measured in the Part A ester solution) was added and the mixture was cooled to about 0° C. While maintaining the temperature below 5° C., methanesulfonyl chloride (2.02 g, 17.6 mmol, plus approximately 0.4 mmol per mmol of water measured in the Part A ester solution) was added. The reaction mixture was stirred at about 5° C. for about 5 hours. The mixture was warmed to about 25° C. and stirred for about 20 hours. Cold (about 5° C.) water was added while maintaining the pH at about 8.0 by the addition of aqueous phosphoric acid. The resulting suspension was stirred at about 10° C. for about 1 hour. The product was collected and the cake was washed with cold (about 5° C.) water. The product was dried under vacuum at about 25° C. to afford title compound.

C. [1S-(1α,2α,4,5α)]-2-[[3-[4-[(Pentylamino)carbonyl]-2-oxazolyl]-7-oxabicyclo[2.2.1]hept-2-yl]methyl]benzenepropanoic acid, methyl ester Under an inert atmosphere, hexamethylenetetramine (5.89 g, 42.0 mmol) was added to a mixture of copper(II) bromide (8.63 g, 38.6 mmol) and methylene chloride. A solution of 1,8-diazabicyclo[5.4.0]undec-7-ene (6.38 g, 41.9 mmol) in methylene chloride was added with slight cooling to maintain the temperature at about 30° C. A solution of Part B ester (4.50 g, 9.86 mmol) in methylene chloride was added, and the reaction mixture was stirred at about 30° C. for about 14 hours. The mixture was cooled to about 20° C. and filtered, and the cake was washed with methylene chloride. At this point, the filtrate may be combined with the filtrate from another run. The filtrate was concentrated under vacuum at about 30° C., and ethyl acetate, water and aqueous ammonia were added to the resulting residue. The phases were separated, and the organic phase was washed with a mixture of water and aqueous ammonia. The resulting aqueous solution was back extracted with ethyl acetate. The combined organic phase was washed sequentially with aqueous phosphoric acid and brine. Brine was added to the organic phase and the pH was adjusted to about 7 with saturated sodium bicarbonate. The organic solution was separated and partially concentrated under vacuum at about 40° C. Seed crystals of title compound were added followed by n-heptane. The remaining ethyl acetate was replaced with n-heptane by a vacuum-distillation exchange procedure at a temperature of 40° C. or below. The product was collected and the cake is washed with n-heptane. The product was dried under vacuum at about 25° C. to afford title compound.

D. [1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, monosodium salt Under an inert atmosphere, 1N sodium hydroxide (3.6 mL, 3.6 mmol) was added to a cold (about 5° C.) solution of Part C ester (0.600 g, 1.32 mmol) in tetrahydrofuran. The reaction mixture was stirred at about 25° C. for about 4 hours. The reaction mixture was partially concentrated under vacuum at about 35° C. The concentrated solution was diluted with water and then washed with diethyl ether. The phases were separated and the pH of the aqueous solution was adjusted to about 7 with concentrated hydrochloric acid. Methylene chloride was added and acidification was continued with stirring to a pH of about 2. The phases were separated and the aqueous layer was extracted with methylene chloride. The resulting combined organic extract was washed sequentially with water and brine. The organic solution was dried over anhydrous magnesium sulfate, filtered and concentrated under vacuum at about 25° C. to a solid. The resulting solid was dissolved in hot (about 90° C.) acetonitrile, and the solution was allowed to stand at room temperature without stirring for about 12 hours. The product was collected and the cake was washed with cold (about 5° C.) acetonitrile. The product was dried under vacuum at about 35° C. to afford title compound.

Under an inert atmosphere, title compound (461 g, 1.04 mol) was dissolved in acetone at about 50° C. The resulting solution was cooled to about 35° C. and a solution of 25% w/w sodium methoxide in methanol (0,264 mL, 1.15 mol) was added. The resultant slurry was allowed to cool to about 25° C. with stirring. The product was collected and the cake was washed with acetone. The product was dried under vacuum at about 35° C. to afford title compound.

EXAMPLE 6

(S)-(−)-α-Methylbenzylmaleimide

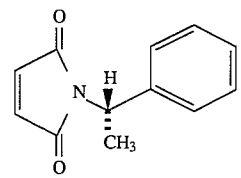

A. (S)-(−)-α-Methylbenzylmaleamic acid

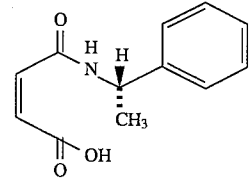

| Material | F.W. | Moles | Equiv. | Amount |
|---|---|---|---|---|
| Maleic Anhydride | 98.06 | 0.102 | 1.0 | 10.00 g |
| MBA* | 121.18 | 0.107 | 1.05 | 13.80 ml |
| Acetonitrile | — | — | — | 100.0 ml |

*(S)-(−)-α-methylbenzylamine

A 250 mL three-necked flask fitted with mechanical stirrer, condenser and thermocouple was charged with maleic anhydride and acetonitrile.

The (S)-(−)-α-methylbenzylamine was added dropwise via an addition funnel (over a fifteen minute period) with stirring to the maleic anhydride solution. The reaction was complete in three hours according to HPLC to form title compound.

B. (S)-(−)-α-Methylbenzylmaleimide

| Material | F.W. | Moles | Equiv. | Amount |
|---|---|---|---|---|
| Part A Maleamic acid | | — | 1.0 | 100.0 ml approx. |
| Diisopropylamine | 101.19 | 0.204 | 2.0 | 28.58 ml |
| HMDS* | 161.14 | 0.204 | 2.0 | 43.00 ml |

*1,1,1,3,3,3-Hexamethyldisilazane

Diisopropylamine was added to the stirring colorless reaction solution via an addition funnel followed by a rapid addition of the HMDS.

The reaction solution was heated to reflux (76.0° C.) and refluxing was maintained for 18 hours. The reaction solution changed from a colorless solution to a dark wine solution. The reaction was judged complete via HPLC to form title compound.

The reaction solution was allowed to cool to room temperature and the acetonitrile was removed in vacuo giving a wine colored oil. Ethanol (50 ml) and 1N HCl (50 ml) were added to the oil and the solution was stirred at 45° C. for ten minutes. The ethanol was removed in vacuo and the wine solution was extracted with methylene chloride (100 ml). The organic layer was washed with saturated sodium bicarbonate (50 ml), brine (50 ml) and dried over anhydrous magnesium sulfate. The methylene chloride was removed in vacuo to give a dark wine oil (13.09 g, 63.8M % yield). This oil was purified on a pad of silica gel eluting with hexane/ethyl acetate 7:3 to give title compound in the form of a pale amber oil (10.71 g, 52.2M % yield).

EXAMPLE 7

[2(S),3aα,4β,7β,7aα]-Hexahydro-2-(1-phenylethyl)-4,7-epoxy-1H-isoindole-1.3(2H)-dione AlCl$_3$ (0.199 g, 1.49 mM) was added to Example 6 imide (1.0 g, 4.98 mM) and furan (1.08 ml, 14.9 mM) stirred in CH$_2$Cl$_2$ (16.6 ml) chilled in an ice bath under an argon atmosphere. After 15 min the ice-bath was removed and the mixture was stirred overnight at room temperature. A black precipitate was formed. TLC (silica gel, EtOAc-Hexane 1:1, visualized by UV and ceric ammonium molybdate) showed disappearance of the imide R$_f$ 0.71 and appearance of the title compound at R$_f$ 0.44. EtOAc (20 ml) and 1N HCl (20 ml) were added and stirred for 10 min. The mixture was filtered through Celite to remove a brown solid which was washed on the filter with EtOAc (100 ml). The filtrate was added to a separatory funnel, the aqueous layer separated, and the organic layer washed with 1N HCl (20 ml), water (20 ml), 5% NaHCO$_3$ (20 ml), brine (10 ml), and dried (MgSO$_4$ for 5 min). Darco G-60 (0.5 g) was added and stirred for 30 min. The mixture was filtered through Celite and evaporated to ~25 ml. The residue was washed with 25 ml EtOAc into a hydrogenation flask containing 5% Pd/C (0.1 g). H$_2$ was sparged through the mixture for 1 hr. N$_2$ was sparged for 15 min. to remove excess H$_2$. Darco G-60 (0.5 g) was added and stirred for 30 min. The mixture was filtered through Celite, washed with EtOAc, and evaporated: 1.27 g (94% crude yield).

The semisolid residue was dissolved in EtOAc (1.5 ml) and heptane (10 ml) by heating on the steam bath. The solution was let stand at room temperature for 2 hrs and at 0° for 3 hrs. The crystals were filtered, washed with cold hexane and dried overnight under vacuum to yield 1.12 g (83%) of title compound, mp. 107°–9°.

Anal. calcd. for C$_{16}$H$_{17}$NO$_3$ (271.3) C, 70.83; H, 6.32; N, 5.16; H$_2$O 0.00 Found: C, 70.88; H, 6.25; N, 5.19; H$_2$O 0.01 (KF)

The title intermediate is employed to prepare the aldehyde as described in Example 2.

EXAMPLE 8

(S)-(−)-α-Methylbenzylmaleimide

The title compound (S)-(−)-α-methylbenzylmaleimide was readily obtained from (S)-(−)-α-methylbenzylmaleamic acid.

| Material | F.W. | Moles | Equiv. | Amount |
|---|---|---|---|---|
| Maleamic acid | 219.24 | 0.245 | 1.0 | 53.8 g |
| HMDS* | 161.40 | 0.758 | 3.1 | 160.0 ml |
| Acetonitrile | — | — | — | 1500 ml |

*1,1,1,3,3,3-Hexamethyldisilazane

A 2000 mL three necked flask fitted with mechanical stirrer, condenser and thermocouple was charged with 53.8 grams of Example 6 Part A maleamic acid, 1500 mls. of acetonitrile and 160 ml. of HMDS.

The above solution was refluxed for 48 hours. The reaction was judged to be complete by the absence of starting maleamic acid by HPLC.

The pink reaction solution was cooled to room temperature and acetonitrile was removed in vacuo. The resulting oil was dissolved in ethyl acetate (500 mls) and washed with 50 mls. of a 1N HCl solution followed by 100 mls. of a saturated bicarbonate solution. The rich organic layer was washed with a saturated brine solution and dried over magnesium sulfate. The removal of the ethyl acetate in vacuo afforded 36.0 grams of title compound, 72.9M % yield.

The title compound is employed to prepare the Example 2 aldehyde employing the procedures of Examples 7 and 2.

What is claimed is:

1. A method for preparing a homochiral maleimide intermediate of the structure

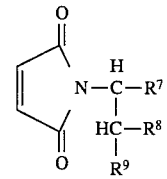

wherein

R$^7$ is aryl or lower alkyl,

R$^8$ is H, aryl or alkyl, and

R$^9$ is H, OH or alkyl, wherein aryl refers to a monocyclic or bicyclic aromatic group containing from 6 to 10 carbons in the ring and alkyl contains 1 to 18 carbons, which comprises (a) providing an amine of the structure

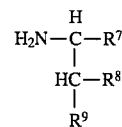

wherein R$^7$, R$^8$ and R$^9$ are as defined above, and (b) treating the amine with maleic anhydride, employing a molar ratio of maleic anhydride: amine of within the range of from about 0.9:1 to about 1.05:1, to form an amide acid, and reacting the amide acid with a silylating agent and an amine base at a temperature within the range from about 60° to about 110° C., to form the maleimide intermediate, the silylating agent being employed in a molar ratio to amide acid within the range of from about 2:1 to about 1:1; and the amine base being employed in a molar ratio to amide acid within the range from about 1.2:1 to about 1:1.

2. The method as defined in claim 1 wherein reaction of the amine with maleic anhydride forms an amide acid of the structure

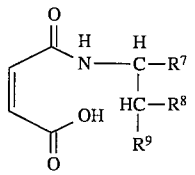

which is reacted with the silylating agent in the presence of an amine base to form the maleimide intermediate.

3. The method as defined in claim 1 wherein the starting amine has the structure

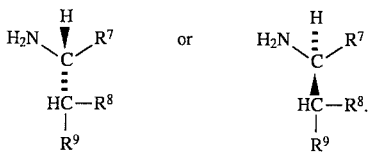

4. The method as defined in claim 3 wherein the starting amine has the structure

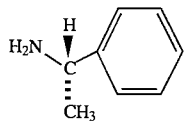

and is reacted with maleic anhydride in the presence of acetonitrile.

5. The method as defined in claim 2 wherein the amide acid has the structure

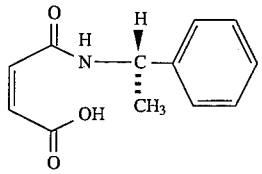

and is reacted with the silylating agent and amine base at a temperature within the range of from about 70° to about 100° C.

6. The method as defined in claim 5 wherein the amine base is diisopropylamine and the silylating agent is 1,1,1,3,3,3-hexamethylsilazane (HMDS).

7. The method as defined in claim 1 wherein the organic base is diisopropylamine, triethylamine, tributylamine or diisopropylethylamine.

8. The method as defined in claim 1 wherein the silylating agent is 1,1,1,3,3,3-hexamethylsilazane (HMDS), chlorotrimethylsilane (TMSCl), 1,3-bis(trimethylsilyl)urea (BSU) or bissilylacetamide (BSA).

9. The method as defined in claim 1 wherein the maleimide intermediate prepared has the structure

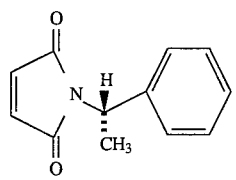

* * * * *